United States Patent [19]

Bridges et al.

[11] Patent Number: 5,525,625
[45] Date of Patent: Jun. 11, 1996

[54] 2-(2-AMINO-3-METHOXYPHENYL)-4-OXO-4H-[1]BENZOPYRAN FOR TREATING PROLIFERATIVE DISORDERS

[75] Inventors: Alexander J. Bridges, Saline; Alan R. Saltiel, Ann Arbor, both of Mich.

[73] Assignee: Warner-Lambert Company, Morris Plains, N.J.

[21] Appl. No.: 378,131

[22] Filed: Jan. 24, 1995

[51] Int. Cl.$^6$ .......................... A61K 31/35; C07D 311/30
[52] U.S. Cl. ................................. 514/456; 549/403
[58] Field of Search ..................... 549/403; 514/456

[56] References Cited

U.S. PATENT DOCUMENTS 3,816,466  6/1974  Strandtmann et al. .
5,116,954  5/1992  Briet et al. .

OTHER PUBLICATIONS

J. Med. Chem., 1991, 34, pp. 798–806, Cushman et al.
Anti-Cancer Drug Design, 1992, 7, pp. 365–384, Cunningham et al.
Acta Chemica Scandinavica, 1965, 19, pp. 823–832, Moses et al.

Primary Examiner—Nicky Chan
Attorney, Agent, or Firm—Charles W. Ashbrook

[57] ABSTRACT

2-(2-Amino-3-methoxyphenyl)-4-oxo-4H-[1]benzopyran inhibits MEK and, as such, is effective in treating cancer and other proliferative diseases such as psoriasis and restenosis.

8 Claims, No Drawings

2-(2-AMINO-3-METHOXYPHENYL)-4-OXO-4H-[1]BENZOPYRAN FOR TREATING PROLIFERATIVE DISORDERS

TECHNICAL FIELD

The present invention relates to a flavone compound which inhibits the dual specificity kinase MEK, and which consequently blocks the proliferation of transformed cells, especially those transformed by the human oncogene Ras.

BACKGROUND OF THE INVENTION

Cancer is generally a disease of the intracellular signalling system, or signal transduction mechanism. Normal cells respond to many extracellular sources, by proliferating or otherwise altering their metabolic activity. The signal transduction system receives such signals at the cell surface, and translates them into a message, decipherable by the cell for subsequent regulation of processes in cytoplasmic, nuclear, cytoskeletal, and membrane biochemistry. Cancer is commonly caused by a series of defects in these signalling proteins, resulting from a change either in their intrinsic activity or in their cellular concentrations. Frequently, these defects lead to a constituitive state whereby the cell nucleus receives an inappropriate signal to proliferate. This can occur through a variety of mechanisms. The cell may produce a growth factor that binds to its own receptors, resulting in an autocrine loop, which continually stimulates proliferation. Mutations can occur in the cell surface (tyrosine kinase) receptors, leading to activation of the kinase in the absence of ligand. Alternatively, many surface kinases can be overexpressed on the cell surface leading to an inappropriately strong response to a weak signal. Mutation or overexpression of many intracellular signalling proteins can lead to similar spurious mitogenic signals arising in the cell. Some of the most common of these mutations occur in the genes encoding the Ras protein, a G-protein which is activated when it is bound to GTP, and inactivated when it is bound to GDP.

The above mentioned growth factor receptors, and many other mitogenic receptors, when activated, lead to Ras being converted from the GDP-bound state to the GTP-bound state. This signal is an absolute prerequisite for proliferation in most cell types. Defects in this signalling system, especially in the deactivation of the Ras.GTP complex, are common in cancers, and lead to the signalling cascade below Ras being chronically activated.

Activated Ras leads in turn to the activation of a cascade of serine/threonine kinases. One of the groups of kinases known to require an active Ras.GTP for its own activation is the Raf family. These in turn activate Mek, which then activates MAP kinase. Activation of MAP kinase by mitogens appears to be essential for proliferation, and constituitive activation of this kinase is sufficient to induce cellular transformation. Blockade of downstream Ras signalling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold, and it can now catalyze the phosphorylation of a large number of proteins, including several transcription factors and other kinases. Many of these MAP kinase phosphorylations are mitogenically activating for the target protein, whether it be another kinase, a transcription factor, or other cellular protein. MEK is also activated by several kinases other than Raf-1, including MEKK, and itself appears to be a signal integrating kinase. As far as is currently known, MEK is highly specific for the phosphorylation of MAP kinase. In fact, no substrate for MEK other than MAP kinase has been demonstrated to date, and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found This invention provides a compound which is a highly specific inhibitor of the MEK kinase activity. Both in enzyme assays and whole cells, the compound inhibits the phosphorylation of MAP kinase by MEK, thus preventing the activation of MAP kinase in cells in which the Ras cascade has been activated. The results of this enzyme inhibition include a reversal of transformed phenotype of some cell types, as measured both by the ability of the transformed cells to grow in an anchorage-independent manner and by the ability of some transformed cell lines to proliferate independently of external mitogens.

The highly selective MEK inhibitory activity of the compound of the current invention is unexpected for several reasons. First, the compound is a member of the class of compounds known as the flavones, many of which are indiscriminate inhibitors of large numbers of protein kinases, so the degree of selectivity of this compound is unexpected. For example, Cushman, et al, *J. Med. Chem.* 1991;34:798–806, describe protein—tyrosine kinase inhibitory activities for a wide variety of flavonoids. Secondly, several close analogues of the invention compound are poor inhibitors of MEK. Lastly, no selective inhibitors of MEK have been reported to date. For example, Cunningham, et al, *Anti-Cancer Drug Design* 1992;7:365–84, Oxford University Press, 1992, describe the activity of several flavones, including a position isomer of the invention compound, which showed little selectivity.

Furthermore, the highly selective effect of the invention compound of the mitogenesis is unexpected. MAP kinase is activated by many cellular stimuli which are not mitogenic, and which mediate nonmitogenic cellular responses. For example, insulin treatment of adipocytes leads to upregulation of glucose transport and both glycogen and lipid synthesis, as well as the upregulation of MAP kinase activity, and it has been assumed that MAP kinase activation is required for the metabolic effects of insulin. The invention compound does inhibit activation of insulin stimulated MAP kinase, but it does not affect insulin-stimulated glucose transport or lipid and glycogen synthesis in murine 3T3-L1 adipocytes, demonstrating that the blockade that it causes can be selective for mitogenic effects over metabolic regulation.

SUMMARY OF THE INVENTION

This invention provides a compound which is 2-(2-amino-3-methoxyphenyl)-4-oxo-4H-[1]benzopyran. The compound has the formula

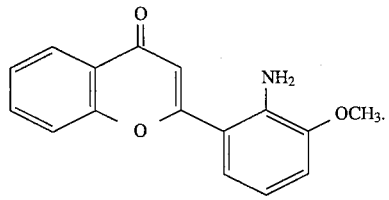

The invention includes the pharmaceutically acceptable acid addition salts and solvates of the benzopyran.

Another embodiment of the invention is a pharmaceutical formulation comprising the benzopyran or pharmaceutically acceptable salt or solvate thereof together with a pharmaceutically acceptable carrier, diluent, or excipient therefor.

A further embodiment is a method for inhibiting MEK dual specificity kinase comprising administering to a mammal an MEK kinase inhibiting amount of the benzopyran.

Still another embodiment of the invention is a method for treating cancer comprising administering to a patient in need of treatment an anticancer amount of a benzopyran of this invention. Also included is a method for treating the proliferative disorders, including, but not limited to psoriasis, restenosis, autoimmune disease, and atherosclerosis.

DETAILED DESCRIPTION OF THE INVENTION

The compound of the invention is 2-(2-amino-3-methoxyphenyl)-4-oxo-4H-[1]benzopyran. As noted above, it is a flavone, and can be named as such, i.e., 2'-amino-3'-methoxyflavone. The compound can be prepared by any of several synthetic methods known in the art for making flavones. For example, U.S. Pat. No. 3,816,466 describes reaction of a 2-hydroxy acetophenone derivative with a benzaldehyde in the presence of a base to afford the corresponding flavone.

The invention compound is preferably prepared by reacting 2-hydroxyacetophenone with a benzoyl chloride, specifically 2-nitro-3-methoxybenzoyl chloride, to provide a propanedione, specifically 1-(2-hydroxy-phenyl)-3-(2-nitro-3-methoxyphenyl)-propane-1,3-dione. The propanedione is readily cyclized to provide a benzopyran, namely 2-(2-nitro-3-methoxyphenyl)-4-oxo-4H-[1]benzopyran. The nitro of the benzopyran derivative group is reduced by catalytic hydrogradation to an amino group to give the invention compound. The general reaction scheme is illustrated below in Scheme I.

SCHEME I

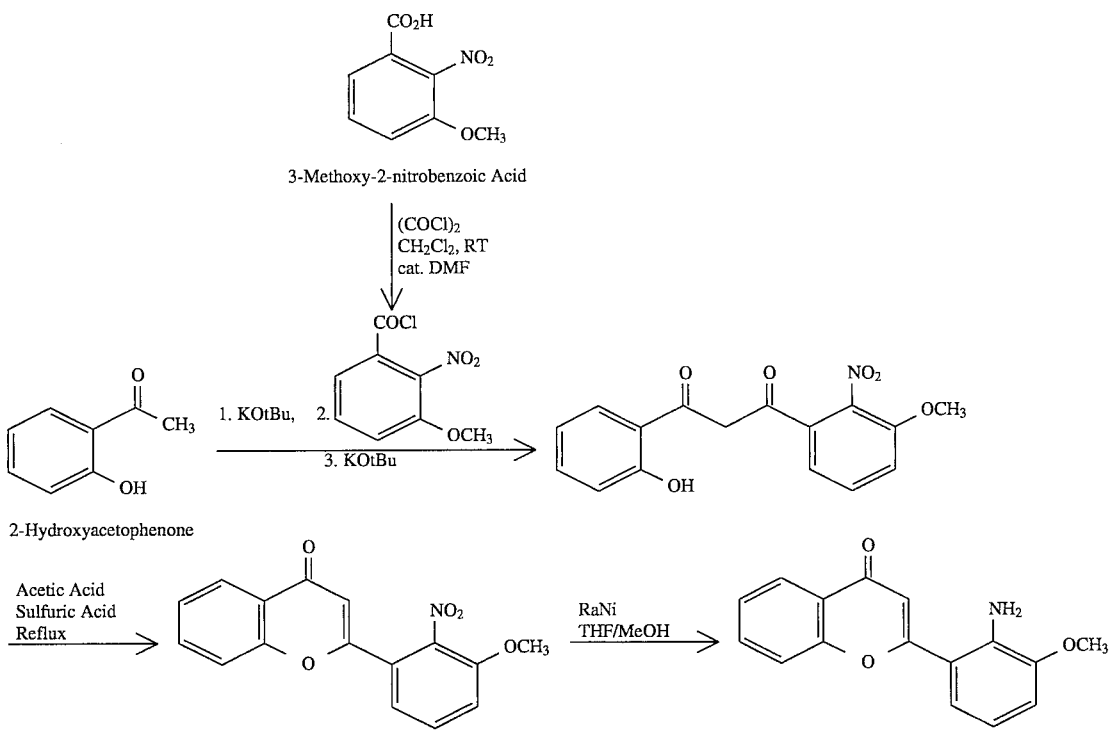

The following detailed examples illustrate the synthesis of the invention compound. The following abbreviations, which are well known to those skilled in the art, are used herein:

| | |
|---|---|
| MEK | Map kinase or Erk Kinase |
| Ras | Rat sarcoma |
| GTP | Guanosine TriPhosphate |
| GDP | Guanosine DiPhosphate |

-continued

| | |
|---|---|
| Raf-1 | A family of three 74–95 kD serine/threonine kinases. |
| Map kinase | Mitogen activated protein kinase. Also called MAP kinase or MAPK. |
| MEKK | MEK Kinase |
| HEPES | 4-(2-Hydroxyethyl)-1-piperazineethane-sulfonic acid |
| EGTA | Ethylenebis(oxyethylenenitrilo)tetraacetic acid |
| ATP | Adenosine TriPhosphate |
| MBP | Myelin Basic Protein |
| Tris | Tris(hydroxymethyl)aminomethane buffer |
| SDS | Sodium Dodecyl Sulfate |
| DMSO | Dimethyl sulfoxide |
| PDGF | Platelet Derived Growth Factor |
| PBS | Phosphate Buffered Saline |
| NGF | Nerve Growth Factor |
| v-Src | The oncogene of the Rous sarcoma virus |
| EGFR | Epidermal Growth Factor Receptor |
| NGFR | Nerve Growth Factor Receptor |
| PDGFRβ | Platelet Derived Growth Factor Receptor β |
| PI-3 kinase | Phosphatidylinositol-3-kinase. |

Preparation of 2-methoxy-2-nitrobenzoyl chloride

Oxalyl chloride (2 mL, 24 mmol) and DMF (0.4 mL) are added to a suspension of 3-methoxy-2-nitro benzoic acid (4 g, 20 mmol) in 200 mL of dichloromethane. The reaction mixture is stirred for 3 hours at 25° C. under nitrogen. The reaction solvents are removed under reduced pressure to yield 3-methoxy-2-nitrobenzoyl chloride (4.3 g, quant.) as a yellow solid. $^1$H NMR (DMSO): δ7.80 (1H, d, J=8 Hz), 7.65 (1H, t, J=9 Hz), 7.42 (1H, d, J=10 Hz).

Preparation of 1-(2-hydroxyphenyl)-3-(3-methoxy-2-nitrophenyl)propane-1,3-dione

To a 300-mL, three-neck, round-bottom flask with a mechanical stirrer is added potassium tert.-butoxide (2.5 g, 22 mmol). The flask is cooled to 0° C. and dry THF (10 mL) is added. To this solution, 2-hydroxy-acetophenone (3.5 mL, 18.6 mmol) in THF (10 mL) is added slowly over 30 minutes keeping the temperature below 5° C. The resulting yellow paste is warmed to 25° C. and stirred for 35 minutes. The mixture is cooled to 0° C. and 3-methoxy-2-nitrobenzoyl chloride (4.3 g, 20 mmol) in THF (15 mL) is added slowly over 15 minutes, keeping the temperature below 5° C. The mixture is warmed to 25° C. and stirred for 1 hour. The mixture is cooled to 5° C. and solid potassium tert.-butoxide (2.5 g, 22 mmol) is added forming a dark brown paste. THF (30 mL) is added and the mixture is heated at reflux for 3 hours. The mixture is cooled to 25° C. and 3N HCl is added until the pH falls to 2. The mixture is concentrated under reduced pressure to leave a brown solid. The brown solid is dissolved in CH$_2$Cl$_2$ (200 mL) and H$_2$O (50 mL), washed with saturated NaHCO$_3$ solution (200 mL), saturated brine (200 mL), and H$_2$O (200 mL). The organic layer is dried (Na$_2$SO$_4$) and concentrated under reduced pressure to yield 1-(2-hydroxyphenyl)-3-(3-methoxy-2-nitrophenyl)propane-1,3-dione (5.52 g, 79%) as a tautomeric mixture.

Preparation of 2-(3-methoxy-2-nitrophenyl)-4-oxo-4H-[1]benzopyran

A solution of glacial acetic acid (15 mL), concentrated sulfuric acid (180 mL), and 1-(2-hydroxy-phenyl)-3-(3-methoxy-2-nitrophenyl)propane-1,3-dione (770 mg, 2.43 mmol) is heated at reflux for 2.5 hours. The hot solution is poured onto crushed ice and H$_2$O (200 mL), stirring vigorously for 30 minutes. The solution is cooled in a refrigerator. The resulting solid is filtered and washed with H$_2$O to yield 2-(3-methoxy-2-nitrophenyl)-4-oxo-4H-[1]benzopyran (510 mg, 70%) as a brown solid.

$^1$H NMR (DMSO): δ8.02 (1H, d, J=8.0 Hz), 7.81 (1H, t, J=6.9 Hz), 7.74 (1H, t, J=8.2 Hz), 7.59 (1H, t, J=8.4 Hz), 7.51 (1H, t, J=7.4 Hz), 7.42 (1H, d, J=8.3 Hz), 6.81 (1H, s), 3.92 (3H, s).

Synthesis of 2-(2-amino-3-methoxy-phenyl)-4-oxo-4H-[1]benzopyran 2-(3-Methoxy-2-nitrophenyl)-4-oxo-4H-[1]benzopyran (1.73 g, 5.8 mmol) in methanol (50 mL) and THF (50 mL) is hydrogenated under pressure with RaNi (0.5 g). The solution is concentrated under reduced pressure and recrystallized from toluene to yield 2-(2-amino-3-methoxyphenyl)-4-oxo-4H-[1]benzopyran (900 mg, 58%) as a solid. $^1$H NMR (DMSO): δ8.07 (1H, d, J=8.0 Hz), 7.83 (1H, t, J=6.9 Hz), 7.70 (1H, d, J=7.7 Hz), 7.51 (1H, t, J=7.0 Hz), 7.09 (1H, d, J=8.0 Hz), 7.00 (1H, d, J=7.0 Hz), 6.71 (1H, t, J=8.0 Hz), 6.56 (1H, s), 5.30 (2H, s), 3.85 (3H, s).

This invention also includes pharmaceutically acceptable acid addition salts of the invention compound. Such salts are prepared by reacting the invention compound with an equimolar quantity of an inorganic acid such as hydrochloric, hydrobromic, sulfuric, phosphoric, and similar inorganic acids. Organic acids can also be utilized to form salts, for example, acetic, lactic, maleic, methanesulfonic, succinic, benzoic, and similar organic acids.

Preferred salts include the hydrochloride and the acetate. Solvates such as hydrates and alcoholates (e.g., with ethanol) can also be used.

The invention compound is useful in treating cancer by virtue of its selective inhibition of the dual specificity protein kinase MEK. The invention compound has been evaluated in a number of biological assays which are normally utilized to establish inhibition of proteins and kinases, and to measure mitogenic and metabolic responses to such inhibition.

Enzyme Assays

Cascade assay for inhibitors of the MAP kinase pathway.

Incorporation of $^{32}$P into myelin basic protein (MBP) was assayed in the presence of a glutathione S-transferase fusion protein containing p44MAP kinase (GST-MAPK) and a glutathione S-transferase fusion protein containing p45MEK (GST-MEK). The assay solution contained 20 mM HEPES, pH 7.4, 10 mM MgCl$_2$, 1 mM MnCl$_2$, 1 mM EGTA, 50 µM [γ-$^{32}$P]ATP, 10 µg GST-MEK, 0.5 µg GST-MAPK and 40 µg MBP in a final volume of 100 µL. Reactions were stopped after 20 minutes by addition of trichloroacetic acid and filtered through a GF/C filter mat. $^{32}$P retained on the filter mat was determined using a 1205 Betaplate. Compounds were assessed at 10 µM for ability to inhibit incorporation of $^{32}$P.

To ascertain whether compounds were inhibiting GST-MEK or GST MAPK, two additional protocols were employed. In the first protocol, compounds were added to tubes containing GST-MEK, followed by addition of GST-MAPK, MBP and [γ-$^{32}$P]ATP. In the second protocol, compounds were added to tubes containing both GST-MEK and GST-MAPK, followed by MBP and [γ-$^{32}$P]ATP. Compounds that showed activity in both protocols were scored as MAPK inhibitors, while compounds showing activity in only the first protocol were scored as MEK inhibitors.

In vitro MAP kinase assay.

Inhibitory activity was also confirmed in direct assays. For MAP kinase, 1 µg GST-MAPK was incubated with 40 µg MBP for 15 minutes at 30° C. in a final volume of 50 µL containing 50 mM Tris (pH 7.5), 10 µM MgCl$_2$, 2 µM EGTA, and 10 µM [γ-$^{32}$P]ATP. The reaction was stopped by addition of Laemmli SDS sample buffer and phosphorylated MBP resolved by electrophoresis on a 10% polyacrylamide gel. Radioactivity incorporated into MBP was determined by autoradiography, and subsequently by excision of the bands followed by scintillation counting.

In vitro MEK assay.

For evaluation of direct MEK activity, 10 µg GST-MEK1 was incubated with 5 µg of a glutathione S-transferase fusion protein containing p44MAP kinase with a lysine to alanine mutation at position 71 (GST-MAPK-KA). This mutation eliminates kinase activity of MAPK, so only kinase activity attributed to the added MEK remains. Incubations were 15 minutes at 30° C. in a final volume of 50 µL containing 50 mM Tris (pH 7.5), 10 µM MgCl$_2$, 2 µM EGTA, and 10 µM [γ-$^{32}$P]ATP. The reaction was stopped by addition of Laemmli SDS sample buffer and phosphorylated GST-MAPK-KA was resolved by electrophoresis on a 10% polyacrylamide gel. Radioactivity incorporated into GST-MAPK-KA was determined by autoradiography, and subsequently by excision of the bands followed by scintillation counting. Additionally, an artificially activated MEK was utilized that contained serine to glutamate mutations at positions 218 and 222 (GST-MEK-2E). When these sites are phosphorylated, MEK activity is increased. Phosphorylation of these sites can be mimicked by mutation of the serine residues to glutamate. For this assay, 5 µg GST-MEK-2E was incubated with 5 µg GST-MAPK-KA for 15 minutes at 30° C. in the same reaction buffer as described above. Reactions were terminated and analyzed as above.

Whole cell MAP kinase assay.

To determine if compounds were able to block activation of MAP kinase in whole cells, the following protocol was used: Cells were plated in multi-well plates and grown to confluence. Cells were then serum-deprived overnight. Cells were exposed to the desired concentrations of compound or vehicle (DMSO) for 30 minutes, followed by addition of a growth factor, e.g., PDGF (100 ng/mL). After a 5-minute treatment with the growth factor, cells were washed with PBS, then lysed in a buffer consisting of 70 mM NaCl, 10 mM HEPES (pH 7.4), 50 mM glycerol phosphate, and 1% Triton X-100. Lysates were clarified by centrifugation at 13,000×g for 10 minutes. Five micrograms of the resulting supernatants were incubated with 10 µg microtubule associated protein-2 (Map2) for 15 minutes at 30° C. in a final volume of 25 µL containing 50 mM Tris (pH 7.4), 10 mM MgCl$_2$, 2 mM EGTA and 30 µM [γ-$^{32}$P]ATP. Reactions were terminated by addition of Laemmli sample buffer. Phosphorylated Map2 was resolved on 7.5% acrylamide gels and incorporated radioactivity determined by autoradiography and subsequent excision of the bands followed by scintillation counting.

When evaluated by the foregoing protocol, the invention compound exhibited an IC$_{50}$ of 7 µM against PC-12 cells stimulated with NGF, and 3 µM against 3T3-L1 cells stimulated with insulin.

Immunoprecipitation and antiphosphotyrosine immunoblots.

To determine the state of tyrosine phosphorylation of cellular MAP kinase, cells were lysed, endogenous MAP kinase was immunoprecipitated with a specific antibody, and the resulting immunoprecipitate analyzed for the presence of phosphotyrosine as follows: confluent cells were serum-deprived overnight and treated with compounds and growth factors as described above. Cells were then scraped and pelleted at 13,000×g for 2 minutes. The resulting cell pellet was resuspended and dissolved in 100 µL of 1% SDS containing 1 mM NaVO$_4$. Following alternate boiling and vortexing to denature cellular protein, 900 µL RIPA buffer (50 mM Tris (pH 7.4), 150 mM NaCl, 1% Triton X-100, 0.1% deoxycholate, and 10 mM EDTA) was added. To this mixture was added 60 µL agarose beads coupled with rabbit immunoglobulin G and 60 µL Pansorbin cells in order to clear the lysate of nonspecific binding proteins. This mixture was incubated at 4° C. for 15 minutes then centrifuged at 13,000×g for 10 minutes. The resulting supernatant was transferred to fresh tubes and incubated with 10 µL of a polyclonal antisera raised against a fragment of MAP kinase for a minimum of 1 hour at 4° C. Seventy microliters of a slurry of agarose beads coupled with protein G and protein A was added and the incubation continued for an additional 30 minutes at 4° C. The beads were pelleted by centrifugation at 13,000×g for 5 minutes and washed 3 times with 1 mL RIPA buffer. Laemmli sample buffer was added to the final bead pellet. This mixture was boiled for 5 minutes then resolved on a 10% acrylamide gel. Proteins on the gel were transferred to a nitrocellulose membrane and nonspecific binding sites on the membrane blocked by incubation with 1% ovalbumin and 1% bovine serum albumin in TBST (150 mM NaCl, 10 mM Tris (pH 7.4), and 0.05% Tween 20). The membrane was then incubated with a commercially available antibody directed against phosphotyrosine. Antibody bound on the membrane was detected by incubation with 125I-protein A, followed by autoradiography.

Cell Growth Assays.

$^3$H-Thymidine incorporation.

Cells were plated in multi-well plates and grown to near confluence. The media was then removed and replaced with growth media containing 1% bovine serum albumin. After 24-hour serum starvation, compounds and specific growth factors were added and incubations continued for an additional 24 hours. During the final 2 hours, 3H-thymidine was added to the medium. To terminate the incubations, the medium was removed and cell layers washed twice with ice-cold phosphate-buffered saline. After the final wash, ice-cold 5% trichloroacetic acid was added and the cells incubated for 15 minutes at room temperature. The trichloroacetic acid solution was then removed and the cell layer washed three times with distilled water. After the final wash, the cell layer was solubilized by addition of 2% sodium dodecylsulfate. Radioactivity in this solution was determined by scintillation counting.

The invention compound showed the following inhibition of PDGF-stimulated thymidine incorporation when evaluated by the foregoing protocol:

| Cell Type | Thymidine Incorporation IC$_{50}$ µM |
| --- | --- |
| Balb 3T3 | 8 |
| K-Balb 3T3 | 10 |

In 3T3-L1 adipocyte cells, in which the inhibition blocks MAPK activation by insulin with an IC$_{50}$ of 3 µM, the compound had no effect on the insulin stimulated uptake of radiolabeled 2-deoxyglucose, or on the insulin-stimulated synthesis of either lipid or glycogen at 10 µM concentration. This demonstrates that the inhibitor shows selectivity between the mitogenic and metabolic effects of insulin, and demonstrates that the inhibitor will show less toxicity than an inhibitor which does not show this surprising selectivity.

Monolayer growth.

Cells were plated into multi-well plates at 10 to 20,000 cells/mL. Forty-eight hours after seeding, compounds were added to the cell growth medium and incubation was continued for 2 additional days. Cells were then removed from the wells by incubation with trypsin and enumerated with a Coulter counter. Growth in soft-agar.

Cells were seeded into 35-mm dishes at 5 to 10,000 cells/dish using growth medium containing 0.3% agar. After chilling to solidify the agar, cells were transferred to a 37° C. incubator. After 7 to 10 days growth, visible colonies were manually enumerated with the aid of a dissecting microscope.

Differential Effect on Cell Types in Anchorage Dependent (Monolayer) Growth and Anchorage Independent (Soft Agar Clonogenicity) Growth Assays.

| Cell Type | Agar Growth IC$_{50}$ μM | Monolayer Growth IC$_{50}$ μM |
|---|---|---|
| K-Ras/Balb | 1.5 | 25 |
| K-Ras/NRK | 2.0 | 40 |
| RSV/RAT-1 | 60 | >100 |
| EGFR/Swiss 3T3 | >100 | >100 |
| K562 | 60 | >100 |
| v-Raf/3Y1 | 4.5 | 50 |

Order of addition experiments established that the inhibitor is inhibiting MEK and not MAP kinase. Experiments looking at the phosphorylation of a kinase defective mutant of MAP kinase as substrate (so that there can be no autophosphorylation of the MAP kinase to complicate interpretation) confirms that the inhibitor inhibits MEK with an IC$_{50}$ essentially identical to that produced in the cascade assay.

The inhibitor does not appreciably inhibit the following kinases at 50 μM concentration.
MAP kinase
  Protein kinase C (rat brain homogenate c-PKC mixture)
  v-Src
  EGFR Tyrosine kinase
  NGFR (trk-A) Tyrosine kinase
  PDGFRβ Tyrosine kinase
  PI-3 kinase
  *E. coli* histidine kinase NRII
  RAF Kinetic analysis demonstrates that the inhibitor is not competitive with ATP. Thus, it does not bind at the ATP binding site of the enzyme, which is probably the explanation as to why this compound does not show the nonspecific kinase inhibitory activity typical of most flavone kinase inhibitors, which do bind at the ATP binding site and which are ATP competitive.

The invention compound will be utilized to treat subjects suffering from cancer and other proliferative diseases and in need of treatment. The compound is ideally suited to treating psoriasis, restenosis, autoimmune disease, and atherosclerosis. The compound will generally be utilized as a pharmaceutical formulation, in which the benzopyran is present in a concentration of about 5% to about 95% by weight. The compound can be formulated for convenient oral, parenteral, topical, rectal, or like routes of administration. The compound will be formulated with common diluents, excipients, and carriers routinely utilized in medicine, for instance, with polyols such as glycerin, ethylene glycol, sorbitol 70; mono- and difatty acid esters of ethylene glycol. Starches and sugars such as corn starch, sucrose, lactose, and the like, can be utilized for solid preparations. Such solid formulations can be in the form of tablets, troches, pills, capsules, and the like. Flavoring agents such as peppermint, oil of wintergreen, and the like can be incorporated.

Typical doses of active benzopyran are those that are effective to treat the cancer or other proliferative disorder afflicting the mammal. Doses will generally be from about 0.1 mg per kilogram body weight to about 50 mg per kilogram body weight. Such doses will be administered from one to about four times a day, or as needed to effectively treat the cancer, psoriasis, restenosis, or other proliferative disorder.

A preferred method for delivering the invention compound is orally via a tablet, capsule, solution, or syrup. Another method is parenterally, especially via intravenous infusion of a solution of the benzopyran in isotonic saline or 5% aqueous glucose.

Following are typical formulations provided by the invention.

| Preparation of 50-mg Tablets | | |
|---|---|---|
| Per Tablet | | Per 10,000 Tablets |
| 0.050 g | 2-(2-amino-3-methoxyphenyl)-4-oxo-4H-[1]benzofuran hydrochloride | 500 g |
| 0.080 g | lactose | 800 g |
| 0.010 g | corn starch (for mix) | 100 g |
| 0.008 g | corn starch (for paste) | 80 g |
| 0.002 g | magnesium stearate (1%) | 20 g |
| 0.150 g | | 1500 g |

The benzopyran, lactose, and corn starch (for mix) are blended to uniformity. The corn starch (for paste) is suspended in 600 mL of water and heated with stirring to form a paste. The paste is used to granulate the mixed powders. The granules are passed through a #8 screen and dried at 120° F. The dry granules are passed through a #16 screen. The mixture is lubricated with 1% magnesium stearate and compressed into tablets.

| Preparation of Oral Suspension | |
|---|---|
| Ingredient | Amount |
| 2-(2-amino-3-methoxyphenyl)-4-oxo-4H-[1]benzopyran monohydrate | 500 mg |
| Sorbitol solution (70% NF) | 40 mL |
| Sodium benzoate | 150 mg |
| Saccharin | 10 mg |
| Red dye | 10 mg |
| Cherry flavor | 50 mg |
| Distilled water qs ad | 100 mL |

The sorbitol solution is added to 40 mL of distilled water and the flavone is suspended therein. The saccharin, sodium benzoate, flavor, and dye are added and dissolved. The volume is adjusted to 100 mL with distilled water. Each milliliter of syrup contains 5 mg of the invention compound. Preparation of Parenteral Solution In a solution of 700 mL of propylene glycol and 200 mL of water for injection is added 20.0 g of 2-(2-amino-3-methoxyphenyl)-4-oxo-4H-[1]benzopyran monoacetate. The volume of the solution is adjusted to 1000 mL by addition of water for injection. The formulation is heat sterilized, filled into 50-mL ampoules each containing 2.0 mL (40 mg of flavone), and sealed under nitrogen.

The invention compound thus formulated will be administered to a mammal in need of treatment for a proliferative disorder such as cancer, psoriasis, restenosis, atherosclerosis, and autoimmune disease at a rate and dose effective to treat the condition. Typical cancers to be treated according to this invention include breast cancer, colon cancer, prostate cancer, skin cancer, and the like. The compound is well-suited to the treatment of psoriasis, restenosis, and atherosclerosis.

We claim:

1. A compound which is 2-(2-amino-3-methoxyphenyl)-4-oxo-4H-[1]benzopyran, or a pharmaceutically acceptable acid addition salt or a solvate thereof.

2. The compound of claim 1 which is a pharmaceutically acceptable salt made with an inorganic acid.

3. The compound of claim 1 which is a pharmaceutically acceptable salt made with an organic acid.

4. A pharmaceutical formulation comprising a compound of claim 1 together with a pharmaceutically acceptable carrier, diluent, or excipient.

5. A method for treating cancer in a mammal comprising administering to a mammal in need of treatment an anticancer effective amount of a compound of claim 1.

6. A method for inhibiting the enzyme Map Kinase or Erk Kinase comprising administering to a mammal a Map Kinase or Erk Kinase inhibiting amount of a compound of claim 1.

7. A method for treating psoriasis comprising administering to a mammal an anti-psoriatic effective amount of a compound of claim 1.

8. A method for treating restenosis comprising administering to a mammal an effective amount of the compound of claim 1.

* * * * *